(12) United States Patent
Yeh et al.

(10) Patent No.: US 8,008,691 B2
(45) Date of Patent: Aug. 30, 2011

(54) ION SENSITIVE FIELD EFFECT TRANSISTOR AND PRODUCTION METHOD THEREOF

(75) Inventors: Jer-Liang Andrew Yeh, Taichung (TW); Shang-Jr Gwo, Hsinchu (TW)

(73) Assignee: National Tsing Hua University

( * ) Notice: Subject to any disclaimer, the term of this patent is extended or adjusted under 35 U.S.C. 154(b) by 282 days.

(21) Appl. No.: 12/506,733

(22) Filed: Jul. 21, 2009

(65) Prior Publication Data

US 2011/0018038 A1    Jan. 27, 2011

(51) Int. Cl.
*G01N 27/403* (2006.01)
(52) U.S. Cl. .......... 257/253; 257/E29.255; 438/49; 438/18; 438/48; 438/422; 438/151; 204/416; 204/433
(58) Field of Classification Search .......... 257/253, 257/E29.255; 438/49, 18, 48, 421, 422, 477, 438/151, 637, 758, 780, 787, 108; 204/416, 204/433
See application file for complete search history.

(56) References Cited

U.S. PATENT DOCUMENTS

| | | | | |
|---|---|---|---|---|
| 5,833,824 | A * | 11/1998 | Benton | 204/416 |
| 7,361,946 | B2 * | 4/2008 | Johnson et al. | 257/253 |
| 7,829,918 | B2 * | 11/2010 | Yeh et al. | 257/253 |
| 2008/0203431 | A1 * | 8/2008 | Garcia et al. | 257/192 |

* cited by examiner

*Primary Examiner* — Zandra Smith
*Assistant Examiner* — Telly Green
(74) *Attorney, Agent, or Firm* — Ming Chow; Sinorica, LLC

(57) ABSTRACT

The present invention discloses an ion sensitive field effect transistor, comprising: a GaN/sapphire layer, used as a substrate; an a-InN:Mg epilayer, deposited on the GaN/sapphire layer, used to provide a current path; a first metal contact, deposited on the a-InN:Mg epilayer to provide drain contact; and a second metal contact, deposited on the a-InN:Mg epilayer to provide source contact; and a patterned insulating layer, used to cover the first metal contact, the second metal contact and the a-InN:Mg epilayer, wherein the patterned insulating layer has a contact window defining an exposure area of the a-InN:Mg epilayer.

15 Claims, 10 Drawing Sheets

ION SENSITIVE FIELD EFFECT TRANSISTOR AND PRODUCTION METHOD THEREOF

BACKGROUND OF THE INVENTION

1. Field of the Invention

The present invention relates to ion sensitive field effect transistors (ISFETs), and more particularly to ion sensitive field effect transistors with a sensitive contact window for detecting the concentration of ions or electrically polarized or charged objects, such as proteins, molecules, e.t.c.

2. Description of the Related Art

The functions of Ion sensitive field effect transistor (ISFET) are based on ion adsorption onto sensing gate which can induce a Helmholtz voltage, modulating the source-drain current. The performance of ISFET is primarily determined by source-drain current/voltage sensitivity or by gate sensitivity at a constant source-drain current. The gate sensitivity means the induced Helmholtz voltage at gate regions with respect to the concentration change (theoretical Nernst constant of 59.16 mV per decade at 25° C.). The current/voltage sensitivity transduces the input gate voltage into the source-drain current. Optimization of the gate sensitivity and the current/voltage sensitivity is crucial for ISFET applications in biomedical and chemical sensing, wherein the current/voltage sensitivity and the gate sensitivity can be influenced by materials or device structures of the ISFET.

The U.S. patents related to the formation of the ISFET are listed hereinafter.

(1) U.S. Pat. No. 4,735,702 discloses a polymer coated on an oxide layer of ISFET, wherein a chemical bond is formed on the interface between the polymer and the oxide layer to form a sensitive film.

(2) U.S. Pat. No. 5,061,976 discloses a method that a carbon thin film is coated on the gate oxide of the ISFET and then a 2,6-xylenol electrolytically polymerized film is coated thereon.

(3) U.S. Pat. No. 5,314,833 discloses a method comprising steps of depositing a silicon film on a GaAs substrate and doping arsenic/phosphorous ions into the silicon film to fabricate the gate with lower resistance.

(4) U.S. Pat. No. 5,319,226 discloses a $Ta_2O_5$ sensing film deposited by a radio frequency sputtering method on an ISFET, wherein the ISFET consists of a $Ta_2O_5/Si_3N_4/SiO_2$ structure.

(5) U.S. Pat. No. 5,387,328 discloses a method of measuring the glucose concentration by fixing the enzyme on a sensing film and using platinum (Pt) as a reference electrode. The sensor has a Pt electrode being capable of sensing all biological substances which generate $H_2O_2$ in enzyme reaction.

(6) U.S. Pat. No. 6,531,858 B2 discloses a method of measuring the hysteresis value and the drift value of an a-Si:H ISFET.

(7) U.S. Pat. No. 6,573,741 B2 a method and an apparatus for measuring the temperature parameters of an ISFET that uses hydrogenated amorphous silicon as a sensing film.

(8) U.S. Pat. No. 6,617,190 B2 discloses an ISFET comprising an $H^+$-sensing membrane consisting of RF-sputtering a-$WO_3$.

(9) U.S. Pat. No. 7,387,923B2 discloses an ISFET using a $PbTiO_3$ layer as a sensing film to detect $H^+$ ions and the fabrication of the $PbTiO_3$ sensing film by a Sol-Gel process.

Recently, group-III nitrides, such as AlGaN, GaN, and InN, are found to exhibit high sensitivity and robust surface properties against the chemical damages. The sensors comprised of III nitride along with electronic readout are noticed to be promising for next generation sensors.

Among group-III nitrides, InN exhibits an unusual phenomenon of strong surface electron accumulation, and has the potential to realize a high current/voltage sensitivity ISFET. The carriers in InN based ISFET transport through surface, bulk and interface channels of the transistors. The carriers in the surface channel are attributed to the surface electron accumulation which is confirmed by various experimental techniques such as capacitance-voltage (C-V) measurements or high-resolution electron-energy-loss spectroscopy (HREELS), etc. The electron accumulation property corresponds to the particularly low conduction band minimum at Γ-point and the Fermi stabilization energy ($E_{FS}$) deep inside the conduction band. The carriers in the interface channel, induced by the band bending of interface polarization charges, depend on the polarity and the lattice mismatch between the InN epilayer and the underlying buffer layer. The sheet carrier density at the polar InN/AlN layer interface is about one order of magnitude higher than that at the nonpolar InN/GaN layer interface due to the differences in spontaneous polarization. The carriers in the bulk channel are of n-type for as-grown undoped InN epilayer, and are probably to be of p-type for Mg-doped InN epilayer. Among the three carrier channels, the surface channel is most adjacent to the layer for ion adsorption, strongly affecting the channel current.

In the present invention, a novel ISFET with a Mg-doped InN (InN:Mg) epilayer is disclosed.

SUMMARY OF THE INVENTION

One objective of the present invention is to provide an ISFET with high current/voltage sensitivity.

Another objective of the present invention is to provide an ISFET with high sensitivity and robust surface against the chemical damages.

Still another objective of the present invention is to provide an ISFET with a concise structure that the current path of the ISFET is implemented with an InN:Mg epilayer.

To achieve the foregoing objectives, the present invention provides an ion sensitive field effect transistor, comprising: a GaN/sapphire layer, used as a substrate; an a-plane Mg-doped InN (a-InN:Mg) epilayer, deposited on the GaN/sapphire layer, used to provide a current path; a first metal contact, deposited on the a-InN:Mg epilayer to provide drain contact; and a second metal contact, deposited on the a-InN:Mg epilayer to provide source contact; and a patterned insulating layer, used to cover the first metal contact, the second metal contact and the a-InN:Mg epilayer, wherein the patterned insulating layer has a contact window defining an exposure area of the a-InN:Mg epilayer.

To make it easier for our examiner to understand the objective of the invention, its structure, innovative features, and performance, we use preferred embodiments together with the accompanying drawings for the detailed description of the invention.

DETAILED DESCRIPTION OF THE PREFERRED EMBODIMENTS

The present invention will be described in more detail hereinafter with reference to the accompanying drawings that show the preferred embodiment of the invention.

Figure 1:
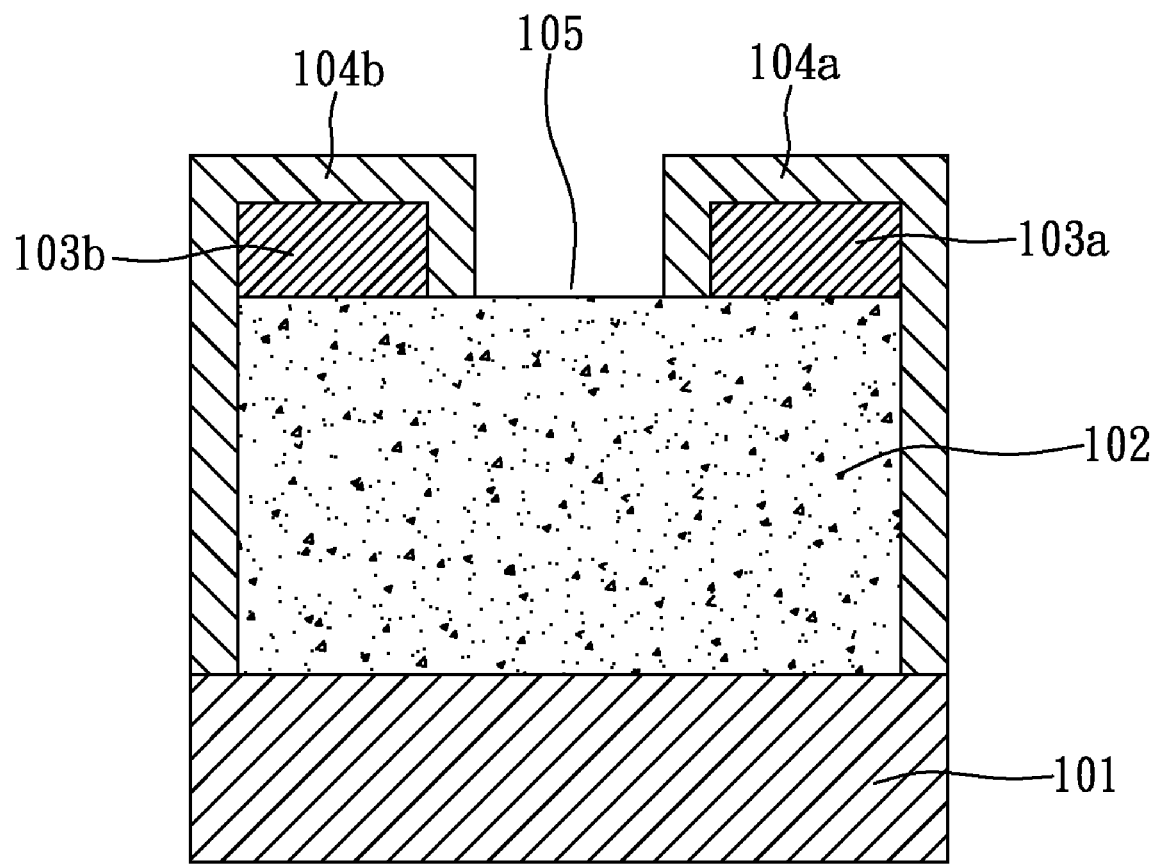
FIG. 1 is a cross-section of an ion sensitive field effect transistor according to a preferred embodiment of the present invention.

Please refer to FIG. 1, which shows a cross-section of an ion sensitive field effect transistor according to a preferred embodiment of the present invention. As shown in FIG. 1, the ion sensitive field effect transistor comprises a GaN/sapphire layer 101, an a-InN:Mg epilayer 102, a metal contact 103a, a metal contact 103b, an insulating layer 104a and an insulating layer 104b.

The GaN/sapphire layer 101 is used as a substrate for the ion sensitive field effect transistor because it has robust surface against chemical damages.

The a-InN:Mg epilayer 102 is an Mg-doped a-plane wurtzite InN layer, used to provide a current path between the metal contact 103a and the metal contact 103b. The a-InN:Mg epilayer 102 has a surface channel, a bulk channel and an interface channel. The surface channel is an ultrathin n type channel of only few nanometers near the surface of the a-InN:Mg epilayer 102, formed due to surface electron inversion, sensitive to the variation of gate bias, so the current path of the ion sensitive field effect transistor is mainly contributed by the surface channel. The bulk channel, of p type, is used to form a depletion region at the interface with the surface channel to isolate the surface channel. The interface channel, of which the carriers are electrons, is formed between the a-InN:Mg epilayer 102 and the GaN/sapphire layer 101, and a depletion region formed thereby between the n type interface channel and the p type bulk channel provides further isolation for the ion sensitive field effect transistor. The thickness of the a-InN:Mg epilayer 102 is preferably but not limited to 1.2 μm for providung a well isolated surface channel.

The metal contact 103a is preferably a structure of Au/Al/Ti (50 nm/200 nm/50 nm), used to provide drain contact of the ion sensitive field effect transistor.

The metal contact 103b is preferably a structure of Au/Al/Ti (50 nm/200 nm/50 nm), used to provide source contact of the ion sensitive field effect transistor.

The insulating layer 104a and the insulating layer 104b are preferably but not limited to 2 μm-thick polyimide layers. A contact window 105 between the insulating layer 104a and the insulating layer 104b defines an exposure area of the a-InN:Mg epilayer 102. The ions in an electrolyte can affect the conductance of the surface channel of the ion sensitive field effect transistor via the contact window 105.

Figure 2:
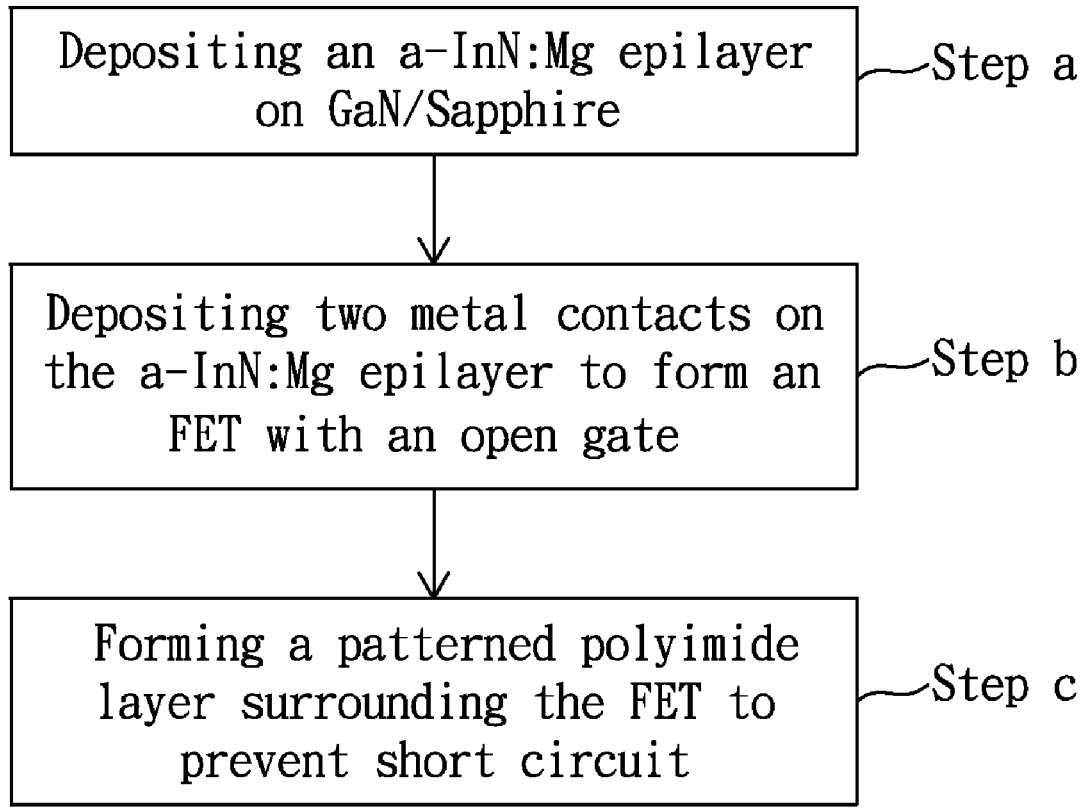
FIG. 2 is a flow chart of an ion sensitive field effect transistor production method according to a preferred embodiment of the present invention.

Please refer to FIG. 2, which shows a flow chart of an ion sensitive field effect transistor production method according to a preferred embodiment of the present invention. As shown in FIG. 2, the production method includes: depositing an a-InN:Mg epilayer on GaN/Sapphire (step a); depositing two metal contacts on the a-InN:Mg epilayer to form an FET with an open gate (step b); and forming a patterned polyimide layer surrounding the ISFET to prevent short circuit.

Figure 3A:
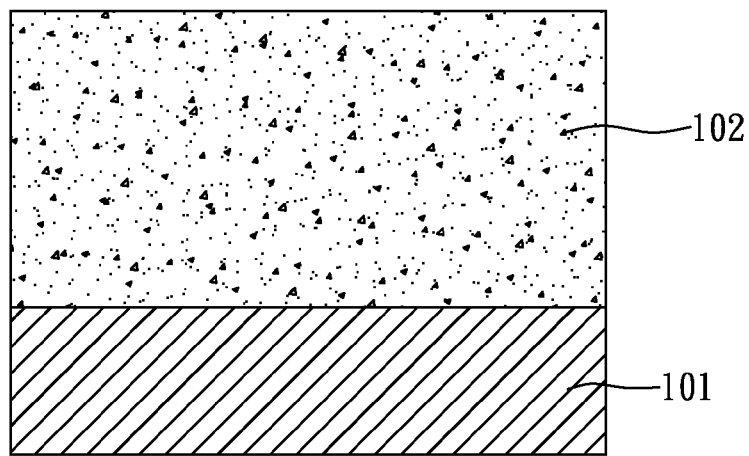
FIG. 3a is a cross-section of the resultant structure of depositing an a-InN:Mg epilayer on GaN/Sapphire using plasma-assisted molecular-beam epitaxy (PAMBE) according to a preferred embodiment of the present invention.

In step a, the a-InN:Mg epilayer, which is an Mg-doped a-plane wurtzite InN layer, is grown on a GaN buffer layer atop a r-plane {1102} sapphire substrate by a plasma-assisted molecular-beam epitaxy (PAMBE) system. As can be seen in FIG. 3a, an a-InN:Mg epilayer 102 is deposited on a GaN/Sapphire layer 101. The thickness of the a-InN:Mg epilayer 102 is preferably but not limited to 1.2 μm for providing a well isolated surface channel.

Figure 3B:
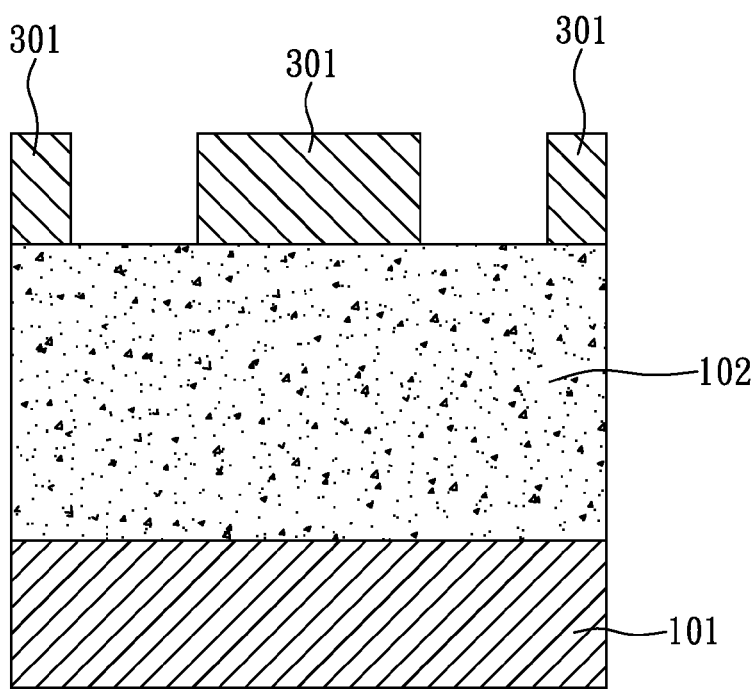
FIG. 3b is a cross-section of the resultant structure of patterning a photoresist layer for metal evaporation according to a preferred embodiment of the present invention.
Figure 3C:
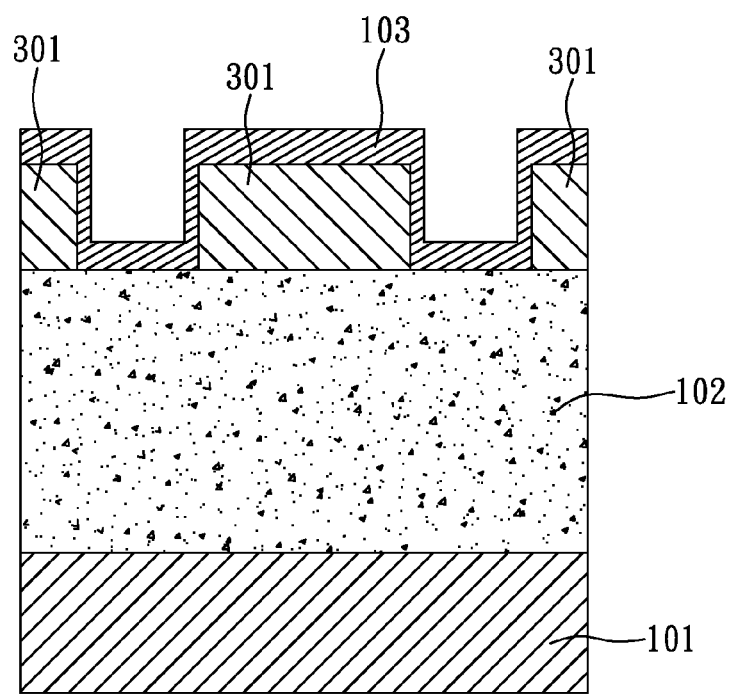
FIG. 3c is a cross-section of the resultant structure of depositing a metal layer according to a preferred embodiment of the present invention.
Figure 3D:
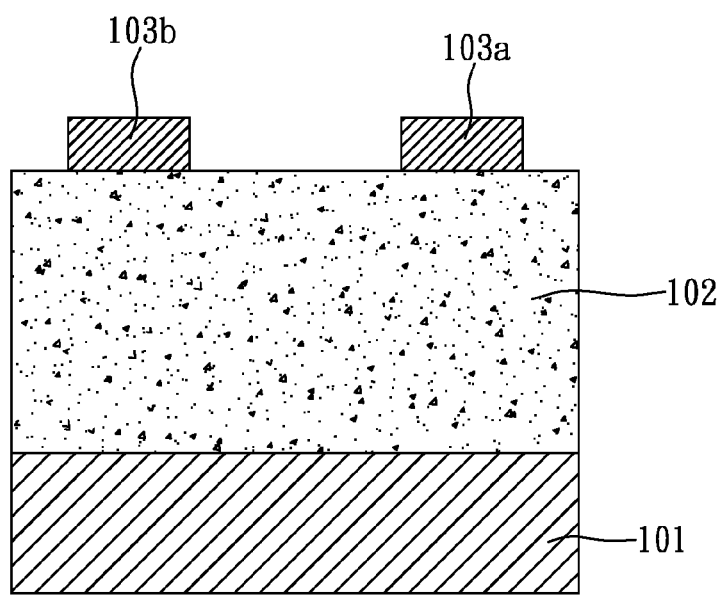
FIG. 3d is a cross-section of the resultant structure of removing the photoresist layer according to a preferred embodiment of the present invention.

In step b, first, as shown in FIG. 3b, a patterned photoresist layer 301, preferably made of AZ4620, is formed on the a-InN:Mg epilayer 102; second, as shown in FIG. 3c, a metal layer 103, preferably but not limited to Au/Al/Ti (50 nm/200 nm/50 nm), is deposited on the patterned photoresist layer 301; and third, as shown in FIG. 3d, a metal contact 103a and a metal contact 103b are formed on the a-InN:Mg epilayer 102 by a lift-off process.

Figure 3E:
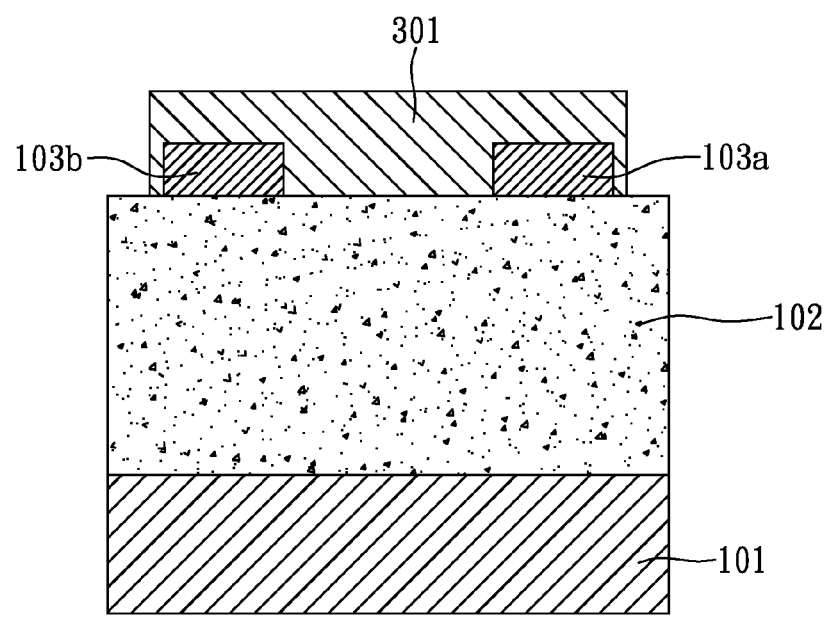
FIG. 3e is a cross-section of the resultant structure of patterning a photoresist layer for an anisotropic etching according to a preferred embodiment of the present invention.
Figure 3F:
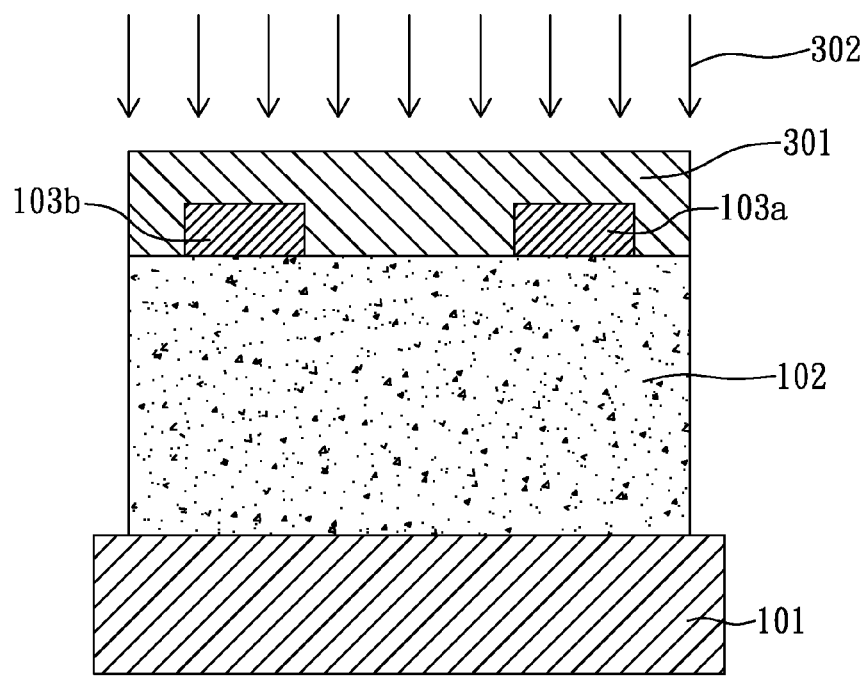
FIG. 3f is a cross-section of the resultant structure of an anisotropic etching on InN by ICP according to a preferred embodiment of the present invention.
Figure 3G:
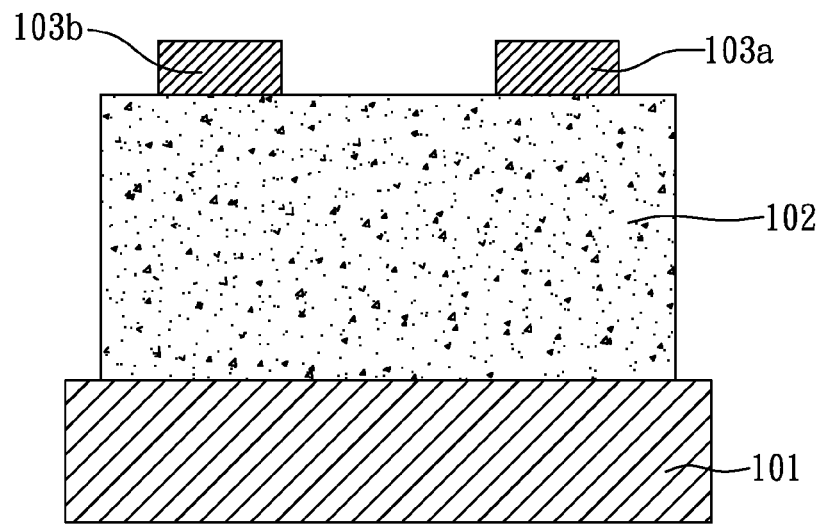
FIG. 3g is a cross-section of the resultant structure of removing the photoresist layer according to a preferred embodiment of the present invention.
Figure 3H:
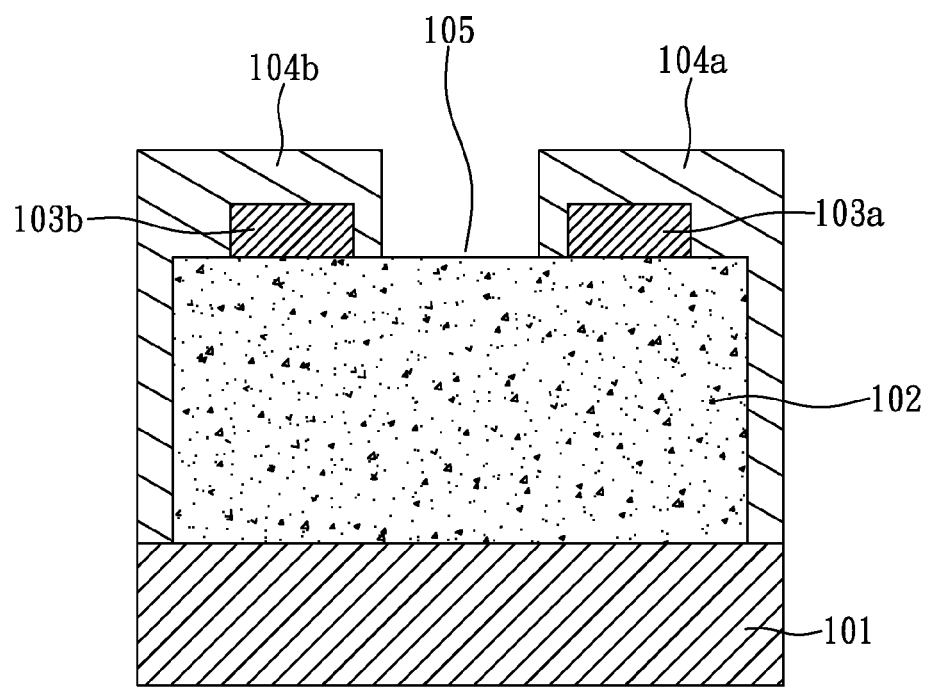
FIG. 3h is a cross-section of the resultant structure of patterning a polyimide layer to define a gate window according to a preferred embodiment of the present invention.

In step c, first, as shown in FIG. 3e, a patterned photoresist layer 301, preferably made of AZ4620, is formed on the metal contact 103a, the metal contact 103b and the a-InN:Mg epilayer 102; second, as shown in FIG. 3f, an anisotropic etching of the a-InN:Mg epilayer 102 is performed by inductively coupled plasma (ICP) 302; third, as shown in FIG. 3g, the patterned photoresist layer 301 is removed; and fourth, as shown in FIG. 3h, a patterned polyimide layer 103a and a patterned polyimide layer 103b are formed to define a contact window 105.

Wafers are diced and the ISFETs are bonded onto carrier boards, for example but not limited to PVC boards, using conducting wires, for example but not limited to aluminum wires, followed by packaging with an insulating material, for example but not limited to polyimethylsiloxane (PDMS).

Figure 4:
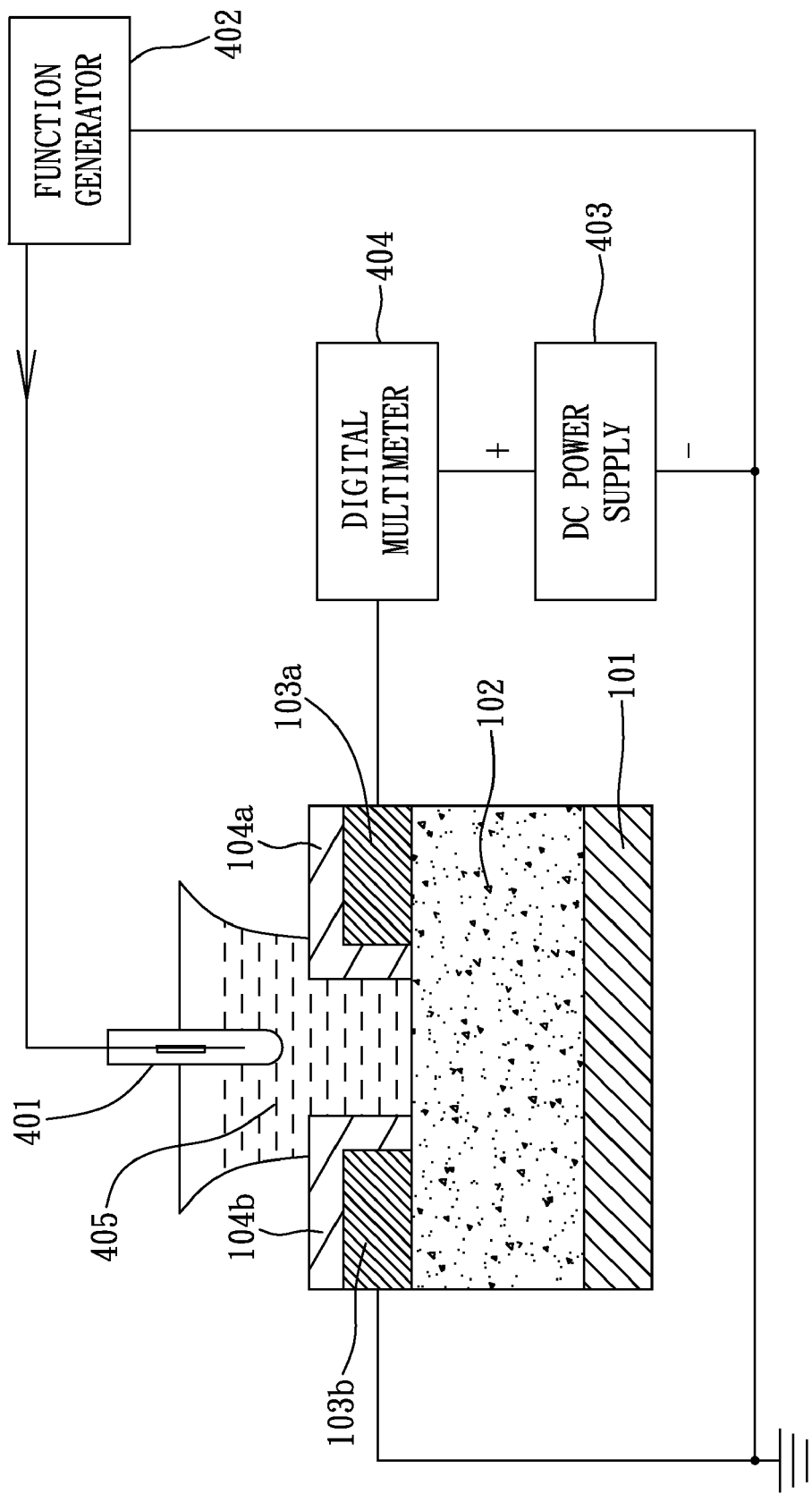
FIG. 4 is a measurement system for a 1.2 μm a-InN:Mg ISFET according to a preferred embodiment of the present invention.

Please refer to FIG. 4, which shows a measurement system for a 1.2 μm a-InN:Mg ISFET according to a preferred embodiment of the present invention. As shown in FIG. 4, the measurement system includes a reference electrode 401, a function generator 402, a DC power supply 403 and a digital multimeter 404.

The reference electrode 401, provided from the function generator 402, preferably made of Hg/HgCl, is immersed in an electrolyte 405 to provide a gate bias voltage.

The function generator 402 is used to provide adjustable DC voltage potential for the reference electrode 401.

The DC power supply 403, with an anode coupled to the metal contact 103a (drain) and a cathode coupled to the metal contact 103b (source), is used to supply a channel current for the ISFET.

The digital multimeter 404, placed between the metal contact 103*b* and the anode, is used to measure the channel current of the ISFET.

Figure 5:
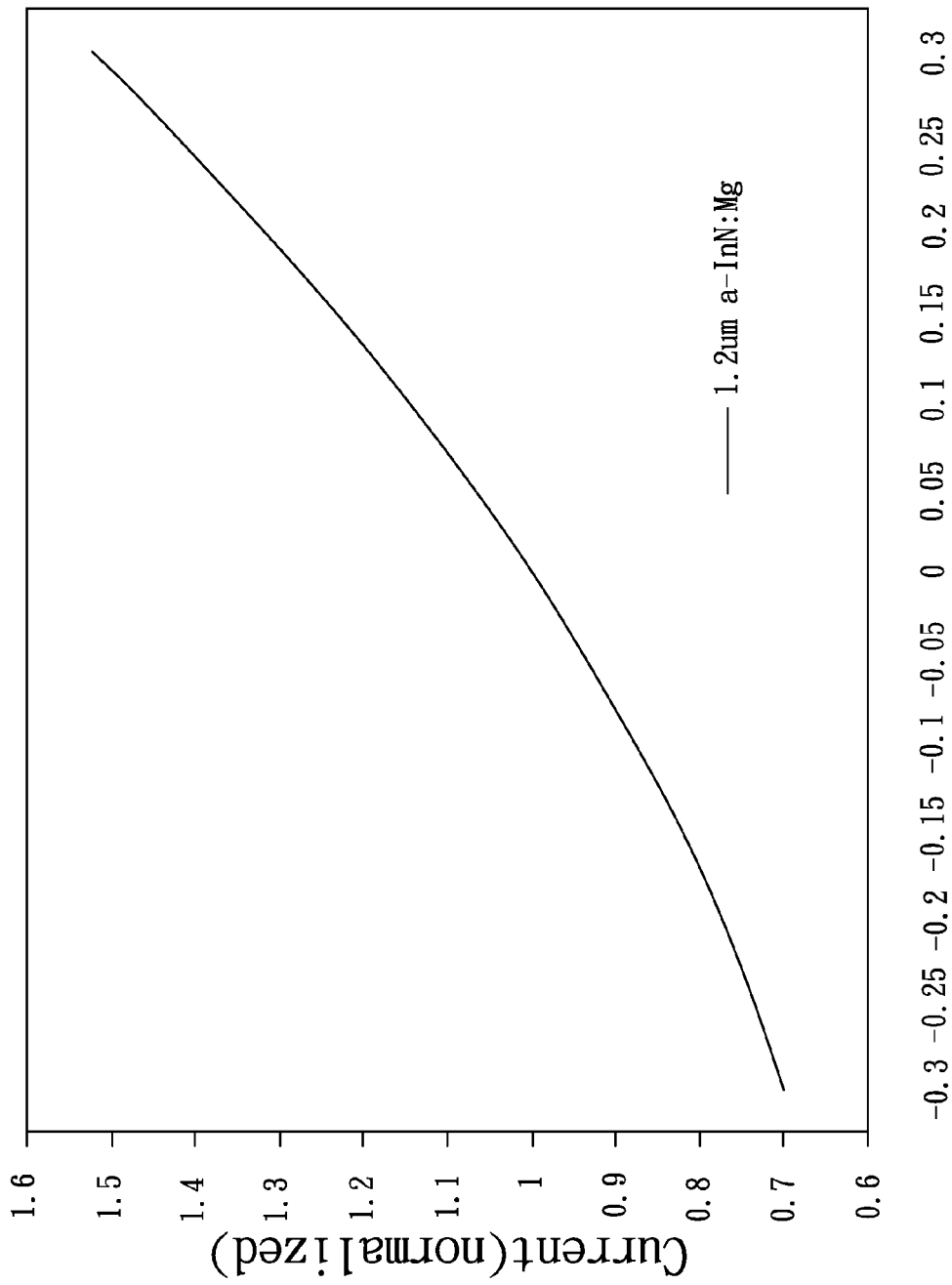
FIG. 5 is the current response of a 1.2 μm a-InN:Mg ISFET to gate bias in a pH 7 buffer solution according to a preferred embodiment of the present invention.

Please refer to FIG. 5, which shows the current response of an a-InN:Mg ISFET to gate bias in a pH 7 buffer solution according to a preferred embodiment of the present invention. As shown in FIG. 5, the drain-source current ($I_{DS}$), normalized to the current at gate bias of 0V, is plotted as a function of gate bias ($V_{GS}$) given a constant drain-source voltage ($V_{DS}$) of 0.25 V while the gate is biased through a pH 7 buffer solution. The current response is 1.52 and 0.7 to gate bias of 0.3 V and −0.3 V, respectively. The a-InN:Mg ISFET has high current/voltage sensitivity because fewer carriers in the interface channel for nonpolar InN/GaN heterointerface are suspected. The surface channel that exists within the topmost few nanometers from the InN surface is easily depleted upon sufficient gate bias. However, the channel current can not be completely suppressed because the carriers at the interface are still electrically connected to the surface possibly through the sidewalls or the dislocation loops in the bulk.

Figure 6:
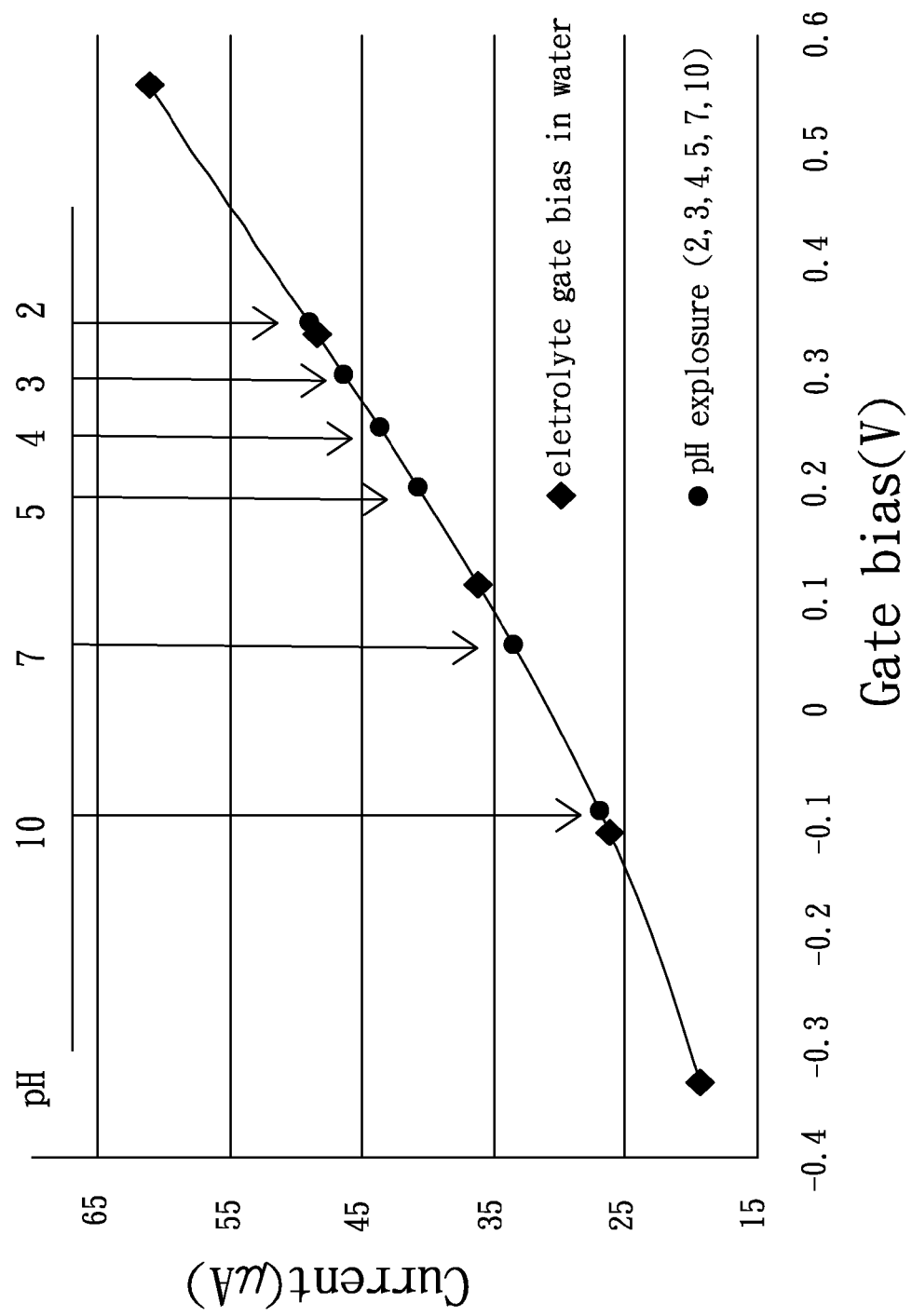
FIG. 6 is an I-V response of an a-InN:Mg ISFET to buffer solutions of pH values from 10 to 2 according to a preferred embodiment of the present invention.

Please refer to FIG. 6, which shows an I-V response of an a-InN:Mg ISFET to electrolyte gate bias in water and different pH buffer solutions (Hanna) of pH values from 10 to 2 according to a preferred embodiment of the present invention. In the measurement, the drain-source voltage ($V_{DS}$) remains unchanged at 0.1V. The current decreases with the decrease of $V_{GS}$ that is used to deplete the surface inversion carriers and hence suppresses the channel current. The measurement result reveals the a-InN:Mg ISFET has a current variation of about 45% at 0.2V compared with 0V, indicating high current/voltage sensitivity characteristics (e.g. sensitive to gate bias). Upon exposure to pH buffer solutions, monotonic currents increase for various pH solutions of from 10 to 2. The average current variation with respect to the pH change per decade is found to be 2.7 μA, corresponding to potential change of 56.5 mV (e.g. a sensitivity of 56.5 mV/pH) based on correlation with the device performance in electrolyte gate bias in water.

Figure 7:
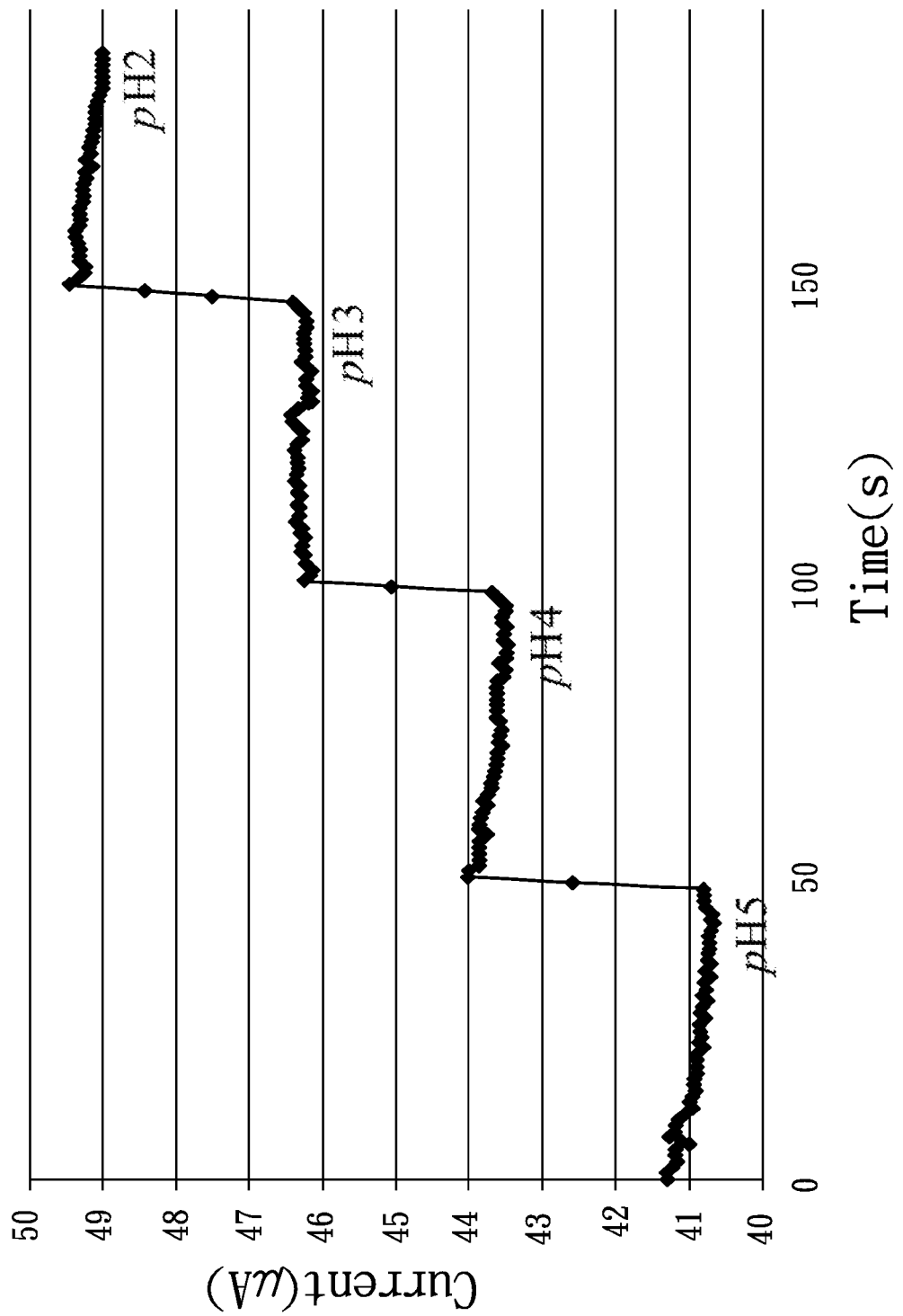
FIG. 7 is a dynamic response of an a-InN ISFET in the buffer solutions with pH values varying from 5 to 2 according to a preferred embodiment of the present invention.

Please refer to FIG. 7, which shows a dynamic response of an a-InN ISFET in the buffer solutions with pH values varying from 5 to 2 according to a preferred embodiment of the present invention. The InN ISFET reveals an abrupt current change upon its exposure to different pH buffer solutions. The response time defined here is the time it takes from 10% of the steady-state current increment (or decrement) to 90% upon its exposure to a different pH buffer solution. The response time is measured to be less than 10 s for the a-InN:Mg ISFET.

In summary, The current($I_{DS)-voltage(VGS)}$) characteristics demonstrates the nonpolar a-InN:Mg ISFET has high current/voltage sensitivity. The doping effect and the nonpolar InN/GaN heterointerface effectively decrease the influence of bulk and interface channels on the current variation, increasing the current/voltage sensitivity. As a pH sensor, the a-InN:Mg ISFET show a sensitivity of 56.5 mV/pH and a response time less than 10 s. These results reinforce that the a-InN:Mg ISFET is very promising for a wide variety of chemical and biomedical sensing applications.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures. For example, the substrate can be silicon, r-sapphire, c-sapphire, etc.; the crystal orientation can be c-, a-, m-, etc.; and the thickness can be adjusted.

In summation of the above description, the present invention herein enhances the performance than the conventional structure and further complies with the patent application requirements and is submitted to the Patent and Trademark Office for review and granting of the commensurate patent rights.

What is claimed is:

1. An ion sensitive field effect transistor, comprising:
   a substrate;
   a Mg-doped InN (a-InN:Mg) epilayer, deposited on said substrate, used to provide a current path;
   a first conductive contact, deposited on said InN:Mg epilayer to provide drain contact; and
   a second conductive contact, deposited on said InN:Mg epilayer to provide source contact; and
   a patterned insulating layer, used to cover said first conductive contact, said second conductive contact and said InN:Mg epilayer, wherein said patterned insulating layer has a contact window defining an exposure area of said InN:Mg epilayer.

2. The ion sensitive field effect transistor as claim 1, wherein said substrate is a GaN/sapphire layer.

3. The ion sensitive field effect transistor as claim 1, wherein said conductive contact is made of metal.

4. The ion sensitive field effect transistor as claim 1, wherein said InN:Mg epilayer is an a-InN:Mg epilayer.

5. The ion sensitive field effect transistor as claim 1, wherein said contact window is used to contact with an electrolyte solution.

6. The ion sensitive field effect transistor as claim 1, wherein said first conductive contact is used to couple to a first voltage and said second conductive contact is used to couple to a second voltage to provide a channel current.

7. The ion sensitive field effect transistor as claim 1, wherein said first conductive contact and said second conductive contact include a structure of Au/Al/Ti.

8. The ion sensitive field effect transistor as claim 1, wherein said patterned insulating layer includes polyimide.

9. The ion sensitive field effect transistor as claim 1, wherein said ion sensitive field effect transistor is used for sensing the pH value of an electrolyte solution.

10. An ion sensitive field effect transistor production method, comprising the steps of:
    forming a substrate;
    depositing an InN:Mg epilayer on said substrate;
    depositing a first conductive contact and a second conductive contact on said InN:Mg epilayer to provide drain contact and source contact respectively; and
    forming a patterned insulating layer to cover said first conductive contact, said second conductive contact and said InN:Mg epilayer, wherein said patterned insulating layer has a contact window defining an exposure area of said InN:Mg epilayer.

11. The ion sensitive field effect transistor production method as claim 10, wherein said InN:Mg epilayer is deposited by using a plasma-assisted molecular-beam epitaxy system.

12. The ion sensitive field effect transistor production method as claim 10, wherein said substrate is a GaN/sapphire layer.

13. The ion sensitive field effect transistor production method as claim 10, wherein said conductive contact is made of metal.

14. The ion sensitive field effect transistor production method as claim 10, wherein said InN:Mg epilayer is an a-InN:Mg epilayer.

15. The ion sensitive field effect transistor production method as claim 10, further comprising a step of packaging said ion sensitive field effect transistor with polydimethylsiloxane.

* * * * *